United States Patent
Aloba et al.

(10) Patent No.: US 7,572,779 B2
(45) Date of Patent: Aug. 11, 2009

(54) ORAL PHARMACEUTICAL PRODUCTS CONTAINING 17β-ESTRADIOL-3-LOWER ALKANOATE, METHOD OF ADMINISTERING THE SAME AND PROCESS OF PREPARATION

(75) Inventors: Oluwole T. Aloba, Morristown, NJ (US); Tina M deVries, Long Valley, NJ (US)

(73) Assignee: Warner Chilcott Company LLC, Fajardo, PR (US)

(*) Notice: Subject to any disclaimer, the term of this patent is extended or adjusted under 35 U.S.C. 154(b) by 802 days.

(21) Appl. No.: 10/833,997

(22) Filed: Apr. 29, 2004

(65) Prior Publication Data

US 2004/0209856 A1 Oct. 21, 2004

Related U.S. Application Data

(62) Division of application No. 10/023,748, filed on Dec. 21, 2001, now Pat. No. 6,962,908.

(51) Int. Cl.
*A61K 31/56* (2006.01)
*A01N 25/08* (2006.01)

(52) U.S. Cl. .................. 514/170; 514/178; 514/171; 514/182; 424/409

(58) Field of Classification Search ............... 514/170, 514/171, 178, 182
See application file for complete search history.

(56) References Cited

U.S. PATENT DOCUMENTS

| | | | | |
|---|---|---|---|---|
| 2,156,599 | A | 5/1939 | Scholz | 552/625 |
| 3,478,070 | A | 11/1969 | Stein | 260/397.5 |
| 3,568,828 | A | 3/1971 | Lerner | 206/42 |
| 4,544,554 | A | 10/1985 | Pasquale | 514/170 |
| 5,382,434 | A | 1/1995 | de Haan et al. | 424/465 |
| 5,824,667 | A | 10/1998 | Spona | 514/170 |
| 5,855,906 | A | 1/1999 | McClay | 424/433 |
| 5,928,668 | A | 7/1999 | Greaves et al. | 424/489 |
| 5,976,570 | A | 11/1999 | Greaves et al. | 424/470 |
| 6,200,593 | B1 | 3/2001 | Place | 424/435 |
| 6,221,379 | B1 | 4/2001 | Place | 424/435 |

OTHER PUBLICATIONS

March, Advanced Organic Chemistry, 3rd ed., 1985, p. 334-338.*
Lieveritz, R.W., Amer. J. of Obstetrics and Gynecology, vol. 156, pp. 1289-1293, 1987.
Stumpf, P.G., Obstetrics and Gynecology, vol. 75 (suppl) pp. 9S-17S, 1990.
Marsh, M.S., et al., British Medical Bulletin, vol. 48, pp. 426-457, 1992.
Lobo, R.A., et al., J. of Reproductive Medicine, vol. 37, pp. 77-84, 1992.
Woolfson, D., et al., J. of Controlled Release, vol. 61, pp. 319-328, 1999.
Kuhl, H., Maturitas, vol. 12, pp. 171-197, 1990.
Powers, M., et al., Amer. J. of Obstetrics and Gynecology, vol. 152, pp. 1099-1106, 1985.
Remington: The Science and Practice of Pharmacy, $19^{th}$ ed., 1995, pp. 1413, 1623-1626.
Wolfe et al, Journal of Lipid Research, 2000; 41:368-375.
March, Advance Organic Chemistry, $3^{rd}$ ed., 1985, pp. 334-338.

* cited by examiner

*Primary Examiner*—Sreeni Padmanabhan
*Assistant Examiner*—Sahar Javanmard
(74) *Attorney, Agent, or Firm*—Fitzpatrick, Cella, Harper & Scinto

(57) ABSTRACT

A pharmaceutical dosage unit for oral administration to a human female comprising a therapeutically effective amount of 17β-estradiol-3-lower alkanoate, most preferably 17β-estradiol-3-acetate, and a pharmaceutically acceptable carrier is disclosed. Also disclosed is a method for treating a human female in need of 17β-estradiol and a contraceptive method by oral administration of the pharmaceutical dosage unit and a method of preparing a pharmaceutical composition that may be used to form the pharmaceutical dosage unit of the invention.

5 Claims, No Drawings

ORAL PHARMACEUTICAL PRODUCTS CONTAINING 17β-ESTRADIOL-3-LOWER ALKANOATE, METHOD OF ADMINISTERING THE SAME AND PROCESS OF PREPARATION

This application is a divisional application of U.S. patent application Ser. No. 10/023,348, filed Dec. 21, 2001, the disclosure of which is incorporated by reference herein in its entirety.

BACKGROUND OF THE INVENTION

1. Field of the Invention

This invention relates to a pharmaceutical dosage unit for oral administration containing 17β-estradiol-3-lower alkanoate, most preferably 17β-estradiol-3-acetate, that unexpectedly provides improved bioavailability of estrogen when orally administered to a human female in need of estrogen replacement therapy or receiving estrogen for contraceptive purposes. The invention also relates to a process for producing the pharmaceutical dosage unit.

2. Related Background Art

In the normal, healthy human female, 17β-estradiol is the principal estrogen produced by the functioning premenopausal ovary during each menstrual cycle [Lieveritz, R. W., Amer. J. of Obstetrics and Gynecology, Vol. 156, pp. 1289-1293, 1987]. Estrogen deficiency may occur due to disease, oophorectomy, traumatic injury or as a natural consequence of the aging process. As aging progresses, ovulation becomes less frequent and predictable, resulting in diminished production of 17β-estradiol. Gradual loss of ovarian function occurs naturally around 45-55 years of age leading to the eventual cessation of the menstrual cycle, that is, the menopause.

During normal ovulatory cycles ovarian production of 17β-estradiol ranges from 60-600 μg per day, resulting in circulating levels of 17β-estradiol in serum ranging from 40-400 pg/ml. Circulating 17β-estradiol levels vary during the monthly cycle in the premenopausal woman. At the menopause, when irreversible ovarian failure occurs, 17β-estradiol production decreases dramatically to less than 20 μg per day, giving circulating levels of the hormone in serum of less than 30 pg/ml. [Stumpf, P. G., Obstetrics and Gynecology, Vol. 75 (suppl.) pp. 95-135, 1990]. This low level of estrogen production may result in typical postmenopausal symptoms [Marsh, M. S., et al., British Medical Bulletin, Vol. 48, pp. 426457, 1992]. The physiological consequences of the fall in estradiol levels typically include vasomotor instability (hot flushes), urogenital atrophy and a loss of bone mineral mass leading to osteoporosis.

The most active, naturally occurring human estrogen is unbound 17β-estradiol. Hormone replacement therapy (HRT) seeks to counteract the detrimental effects associated with low circulating plasma estrogen levels by restoring these, as far as possible, to a premenopausal physiological status. It follows, therefore, that the preferential estrogen for HRT is 17β-estradiol and that the aim of HRT is to deliver this hormone at such a rate as to maintain physiological plasma levels of 17β-estradiol.

17β-Estradiol is not absorbed efficiently from the gastric mucosa following administration by the oral route and must, therefore, be formulated for administration in micronized form (to provide an increased surface area) or as a conjugate [Lobo, R. A., et al., J. of Reproductive Medicine, Vol. 37, pp. 77-84, 1992]. The term conjugate encompasses various esters of 17β-estradiol and estrogenic compounds, some of which are derived from equine sources. Examples of conjugates known in the art for the oral administration of estrogen for HRT include estradiol-3,17-diacetate, estradiol-17-acetate, estradiol-3,17-valerate, estradiol-3-valerate, estradiol-17-valerate, ethinyl estradiol, and equine estrogens. The latter are mixtures of estrogens purified from the urine of pregnant mares and containing sulphate and glucouronide derivatives, and equine-specific estrogens such as equilin not normally found in humans [Stumpf, 1990]. In addition, less potent metabolites of 17β-estradiol have been administered by this route, for example, estrone or its conjugates A number of difficulties arise concerning the oral administration of estrogens. Although micronized 17β-estradiol is an efficient form of the natural hormone for its oral administration, micronization represents an additional process for pharmaceutical production, with associated increased costs and inconvenience. Micronized 17β-estradiol has been shown to be equivalent in pharmacokinetic terms to the oral administration of 17β-estradiol valerate, which is metabolised to the parent hormone in vivo. 17β-estradiol valerate is a highly lipophilic ester with no measurable aqueous solubility, as are other ester derivatives of 17β-estradiol administered by the oral route [Woolfson, D., et al., J. of Controlled Release, Vol. 61, pp. 319-328, 1999]. Orally administered 17β-estradiol and its various ester and equine conjugates undergo extensive first-pass hepatic metabolism, resulting in poor bioavailability by the oral route. In addition, hepatic metabolism causes undesirable non-physiological circulating levels of the metabolite estrone and elevation of hepatic proteins. Conjugated equine estrogens, in particular, exert a profound hepatic effect [Kuhl, H., Maturitas, Vol. 12, pp. 171-197, 1990] and are thus clinically less desirable than derivatives of the parent hormone. Oral administration of 17β-estradiol or its conjugates requires a significantly higher dose for clinical efficacy compared to non-oral routes [Powers, M., et al., Amer. J. of Obstetrics and Gynecology, Vol. 152, pp. 1099-1106, 1985].

Much of the prior art literature for preparation of oral pharmaceutical formulations of steroids such as estradiol comprises broad disclosures of solution or suspension wet granulation methods (for example, Pasquale, U.S. Pat. No. 4,544,554; Lerner, U.S. Pat. No. 3,568,828; Greaves, U.S. Pat. No. 5,976,570) or dry mixing using specialized excipients (for example, DeHaan, U.S. Pat. No. 5,382,434; Greaves, U.S. Pat. No. 5,928,668).

Dry mixing of low dose drugs is especially prone to significant lack of uniformity in drug distribution, even with the use of specialized excipients. Wet granulation using organic solvents such as chloroform, as described by Lerner, is generally unacceptable from an environmental, cost, and health and safety standpoint. On the other hand, aqueous wet granulation (e.g. Greaves, U.S. Pat. No. 5,976,570) could readily induce hydrolysis of ester derivatives of 17β-Estradiol. A method for producing uniform, stable orally administered estrogen products with improved bioavailability is therefore highly desirable.

This invention discloses a method for improving the bioavailability of orally administered estrogen in the form of 17β-estradiol-3-lower alkanoate. Parenteral administration of estradiol esters such as estradiol valerate, estradiol cypiorate and estradiol benzoate are well known. 17β-Estradiol-3-acetate has been shown to be an efficient form of estrogen for intravaginal delivery of HRT ([Woolfson et al, 1999], and McClay U.S. Pat. No. 5,855,906), but there has been no disclosure of its surprising advantages when formulated for oral delivery. 17β-Estradiol-3-acetate is known to have an aqueous solubility twice that of 17β-estradiol and vastly greater than that of conventional 17β-estradiol esters such as the valerate, benzoate and 17-acetate esters [Woolfson et al, 1999]. It is well known in the art that esterification of a drug to provide a more lipophilic derivative is a means of improving drug absorption across epithelial membranes, and thus bioavailability. Thus, the highly lipophilic esters of 17β-estradiol are all well known to be absorbed via the oral route, suggesting that the more water-soluble 17β-estradiol-3-acetate would be an unlikely candidate for improving bioavailability of the hormone via the oral route.

SUMMARY OF THE INVENTION

This invention is directed to a pharmaceutical dosage unit for oral administration to a human female comprising a therapeutically effective amount of 17β-estradiol-3-lower alkanoate and a pharmaceutically acceptable carrier. As used herein, lower alkanoate includes formate, acetate and propionate. 17β-estradiol-3-acetate is most preferable. Surprisingly, it has been found that the oral administration of the dosage unit of this invention unexpectedly results in enhanced bioavailability of 17β-estradiol compared to the oral administration of micronized 17β-estradiol or 17β-estradiol-17-valerate. Since it is well known that the lower alkanoate group and in particular the acetate group is readily hydrolyzed upon ingestion, this discovery of improved bioavailability was completely unexpected.

An important aspect of the dosage unit of this invention is that it must be substantially free of ester hydrolysis of the 17β-estradiol-3-lower alkanoate prior to oral administration of the dosage unit. For solid dosage forms, e.g., tablets and capsules, the moisture level in the dosage unit is maintained at a level that substantially inhibits ester hydrolysis of the alkanoate. Generally, the moisture level of the solid dosage unit will be less than 8%. If necessary, the dosage unit may also include an ester hydrolysis inhibitor.

Another embodiment of this invention is directed to a method of treating a human female in need of 17β-estradiol comprising the step of orally administering to the human female a dosage unit comprising a therapeutically effective amount of 17β-estradiol-3-lower alkanoate, preferably 17β-estradiol-3-acetate, and a pharmaceutically acceptable carrier.

A further embodiment of this invention is directed to a method of providing contraception which comprises the step of orally administering to a human female of child bearing age a contraceptive regimen of a daily dosage unit comprising a contraceptively effective amount of 17β-estradiol-3-lower alkanoate, most preferably 17β-estradiol-3-acetate, and a pharmaceutically acceptable carrier. A typical contraceptive regimen is administration of a daily dosage unit for 21 days, although any regimen that provides contraceptive protection is contemplated. Preferably, the dosage unit will contain a combination of a contraceptively effective amount of 17β-estradiol-3-lower alkanoate and at least one progestin.

Due to the enhanced bioavailability of 17β-estradiol obtained when orally administering 17β-estradiol-3-lower alkanoate compared to the oral administration of micronized 17β-estradiol or 17β-estradiol-17-valerate, lesser amounts of the alkanoate need to be administered to achieve the desired therapeutic effect. It is well known that the administration of estrogenic hormones may have significant side effects. Significantly, the methods of this invention allow for 17β-estradiol replacement therapy or contraceptive protection with potentially reduced risk of side effects.

Yet another embodiment of this invention is directed to process of making a pharmaceutical composition containing therapeutic quantities of 17β-estradiol-3-lower alkanoate using a wet granulation process without substantial ester hydrolysis of the alkanoate. This process employees the use of an ester hydrolysis inhibitor.

DETAILED DESCRIPTION OF THE INVENTION

This invention discloses an oral dosage unit of 17β-estradiol-3-lower alkanoate. The alkanoate may be selected from 17β-estradiol-3-formate, 17β-estradiol-3-acetate, 17β-estradiol-3-propionate and mixtures thereof. Most preferably, the 17β-estradiol-3-lower alkanoate is 17β-estradiol-3-acetate.

The oral dosage unit also includes a pharmaceutically acceptable carrier. The term pharmaceutically acceptable in this context refers to a substance having acceptable pharmacological and toxicological properties when administered by the oral route to a person. Such pharmaceutically acceptable carriers are well known.

The oral dosage unit may be of any form suitable for oral administration to a human. Exemplary oral dosage units include, for example, tablets, capsules, powders, chewable tablets, lozenges, troches, sustained or delayed release products or suspensions. More preferably, the oral dosage unit is in the form of a tablet with immediate or sustained release properties. Most preferably, the tablet is formulated for immediate release. Generally, the tablet will contain 17β-estradiol-3-lower alkanoate in an amount of about 0.1 to about 10 mg (as estradiol equivalent). As used herein, estradiol equivalent means that amount of the lower alkanoate that is the molar equivalent of estradiol.

The oral dosage unit is formulated in a manner that substantially prevents the ester hydrolysis of the alkanoate group of the 17β-estradiol-3-lower alkanoate prior to administration. For solid dosage forms, such as tablets, and capsules, the moisture level of the solid dosage unit is generally less than 8% moisture, and preferably less than 5% moisture to help prevent ester hydrolysis prior to administration. For liquid dosage forms, such as suspensions, it is important to stabilize the dosage unit by the addition of an inhibitor of ester hydrolysis. Solid dosage forms may also include an inhibitor of ester hydrolysis.

Optionally, the oral dosage unit may also comprise, in addition to 17β-estradiol-3-alkanoate, other medicament(s) for the treatment or prevention of a human disease. Preferably, the other medicament(s) has a steroidal nucleus (the cyclopentanoperhydrophenanthrene ring system) in its chemical structure, for example, estrogens such as ethinyl estradiol, estrone, mestranol, and esterified estrogens. More preferably, the other medicament(s) has progestational properties and may be selected from progestins such as 3-ketodesogestrel, desogestrel, levodesogestrel, norgestrel, gestodene, mestranol, norethindrone, norethindrone acetate, medroxyprogesterone acetate or similar progestins known in the art. Typical dosages for various progestins are described in the medical literature such as, for example, in the Physician's Desk Reference The pharmaceutically acceptable carrier includes those carriers well known to those skilled in the art used in the formulation of tablets, capsules, and the like. When formulating the dosage unit of this invention, however, it is important to select adjuvants such as fillers, solvents, binders, disintegrants, lubricants and the like that will not cause hydrolysis of the alkanoate esters of the 17β-estradiol-3-lower alkanoate prior to oral administration. Otherwise, the dosage unit of this invention may be prepared in any manner desired. For example, solid dosage units may be prepared by dry blending the ingredients or using a granulation technique followed by tableting or capsule filling techniques well known to those skilled in the art.

In a preferred embodiment of this invention, a pharmaceutical composition containing 17β-estradiol-3-lower alkanoate, most preferably 17β-estradiol-3-acetate and, optionally, other active medicament(s) is prepared using a granulation technique. An aqueous solvent containing a suspending agent and a predetermined amount of at least one pharmaceutically acceptable inhibitor of ester hydrolysis is used as the suspension medium for the preparation of the granules. The suspending agent is used to effect and maintain uniform distribution of 17β-estradiol-3-lower alkanoate and any optional added medicament(s), in the solvent. Following dispersion of 17β-estradiol-3-lower alkanoate and any optional added medicament(s), the suspension is added to suitable pharmaceutical fillers such as lactose and microcrystalline cellulose, then dried to a low moisture content by any suitable method known to those skilled in the art. Optional non-medicated ingredients that may be added to the invention include tablet disintegrants, lubricants, glidants, and colorants. The resultant blend may be compressed into tablets by any suitable means known to those skilled in the art. The pharmaceutical composition prepared according to this invention may also be incorporated into other suitable oral dosage forms, as described hereinbefore.

The term aqueous solvent is used in the context of this invention to denote a water medium and, optionally, a water-miscible solvent such as ethanol or isopropyl alcohol, to support the suspension of the active medicament(s).

Preferably, the amount of the hydrolysis inhibitor incorporated is calculated based on the saturation solubility of the drug in the aqueous solvent. In practice, a stoichiometric excess of the inhibitor is added to the medium in order to push the equilibrium of the reversible esterification-hydrolysis reaction in the direction of the ester, thus maintaining stability of 17β-estradiol-3-lower alkanoate. The pharmaceutically acceptable inhibitor of ester hydrolysis is preferably an organic acid, such as for example, acetic, formic, propionic, lactic or tartaric acid. More preferably, the inhibitor is acetic acid, formic or propionic acid. Most preferably, the inhibitor is acetic acid.

The suspending agent is generally a hydrocolloid that includes water dispersible granulating or binding agents such as polyvinylpyrrolidone; cellulose derivatives such as methylcellulose and hydroxypropylmethylcellulose; polyvinyloxazolidones; gelatin; natural gums such as acacia and tragacanth; starches; sodium alginate; sugars and mixtures thereof.

Suitable pharmaceutical fillers for granulating the prepared drug suspension include, without limitation, lactose, microcrystalline celluloses, dibasic calcium phosphate, starches and mixtures thereof. Optional components of the granulation include pharmaceutically acceptable colorants or other excipients known in the art.

As noted previously, if the dosage unit of this invention takes the form of a tablet or capsule, suitable additional ingredients that may be used include disintegrants such as croscarmellose sodium, starch, sodium carboxymethyl starch, crospovidone, veegum, and lubricants such as hydrogenated vegetable oils, calcium stearate, magnesium stearate, stearic acid, and talc.

In a preferred embodiment of the invention, 17β-estradiol-3-acetate, together with the optional medicament or medicaments, is suspended in an 8% to 12% dispersion of polyvinyl pyrollidone in 95:5 mixture of water and ethanol containing 0.01% glacial acetic acid. The resulting aqueous suspension is blended with carriers and granulated in a granulating vessel. The granulation is dried, screened and blended with disintegrants, glidants, and lubricants. The granulation is then compressed into tablets.

Another embodiment of this invention is directed to a method of treating a human female in need of 17β-estradiol comprising the step of orally administering to said human female a dosage unit comprising a therapeutically effective amount of 17↑-estradiol-3-lower alkanoate, most preferably 17β-estradiol-3-acetate, and a pharmaceutically acceptable carrier. Preferably, the dosage unit is administered to a human female requiring hormone replacement therapy. When used for hormone replacement therapy, the dosage unit of this invention will generally contain 17β-estradiol-3-lower alkanoate in an amount from about 0.1 to about 5 mg (as estradiol equivalent) per dosage unit.

The invention is also directed to a method of providing contraception by orally administering to a human female of child bearing age the dosage unit of this invention containing a contraceptive effective amount of 17β-estradiol-3-lower alkanoate, most preferably 17β-estradiol-3-acetate and a pharmaceutically acceptable carrier. For contraceptive purposes the dosage unit will typically be administered for 21 days, although any dosage regimen that provides contraceptive protection is contemplated. Preferably the contraceptive dosage unit will contain a contraceptive effective amount of 17β-estradiol-3-lower alkanoate, preferably 17β-estradiol-3-acetate, and at least one progestin. Generally, the contraceptive dosage unit of this invention will contain the 17β-estradiol-3-lower alkanoate in an amount from about 0.1 to about 10 mg (as estradiol equivalent) per dosage unit. Typically, the total amount of progestin included in the dosage unit for contraceptive use is in amount from about 20 μg to about 5 mg per dosage unit.

Specific embodiments of the invention will now be demonstrated by reference to the following examples. It should be understood that these examples are disclosed solely by way of illustrating the invention and should not be taken in any way to limit the scope of said invention. Thus, for example, it will be obvious to those skilled in the art that a variety of suitable equipment may be employed to produce the dosage unit of this invention.

EXAMPLE 1

Tablets Containing 17β-Estradiol-3-Acetate

| Ingredient(s) | % w/w | mg/tablet |
| --- | --- | --- |
| 17β-estradiol-3-acetate | 0.500 | 0.450 |
| Colorant | 0.100 | 0.090 |
| Povidone, USP | 1.500 | 1.350 |
| Lactose Monohydrate, NF | 46.949 | 42.254 |
| Microcrystalline Cellulose, NF | 46.949 | 42.254 |
| Croscarmellose Sodium, NF | 3.000 | 2.700 |
| Colloidal Silicon Dioxide, NF | 0.500 | 0.450 |
| Magnesium Stearate, NF | 0.500 | 0.450 |
| Glacial Acetic Acid, USP | 0.002 | 0.002 |
| Alcohol, USP | — | QS |
| Purified Water, USP | — | QS |

Dosage units of the invention in the form of tablets having the above-described constituents are prepared as follows. First, glacial acetic acid, alcohol, and purified water are combined in a suitable vessel to create a granulation solvent. The povidone is dispersed in the granulation solvent, followed by the addition of colorant and 17β-estradiol-3-acetate to the dispersion. The dispersion is slowly sprayed into a blend of the lactose and microcrystalline cellulose. The resulting composition is then dried and milled to form a granulation, which is then combined with the croscarmellose sodium, colloidal silicon dioxide, and magnesium stearate. This blend is then compressed into tablets using appropriate tooling.

EXAMPLE 2

Capsules Containing 17β-Estradiol-3-Acetate and Norethindrone Acetate

| Ingredient(s) | % w/w | mg/tablet |
| --- | --- | --- |
| 17β-estradiol-3-acetate | 1.000 | 0.900 |
| Norethindrone Acetate | 1.000 | 0.900 |
| Povidone, USP | 1.800 | 1.620 |
| Lactose Monohydrate, NF | 58.698 | 52.828 |
| Microcrystalline Cellulose, NF | 35.000 | 31.500 |
| Croscarmellose Sodium, NF | 2.000 | 1.800 |
| Magnesium Stearate, NF | 0.500 | 0.450 |
| Glacial Acetic Acid, USP | 0.002 | 0.002 |
| Alcohol, USP | — | QS |
| Purified Water, USP | — | QS |

Dosage units of the invention in the form of capsules having the above-described constituents are prepared as follows. First, glacial acetic acid, alcohol, and purified water are combined in a suitable vessel to create a granulation solvent. The povidone is dispersed in the granulation solvent, followed by the addition of 17β-estradiol-3-acetate and norethindrone acetate to the resulting dispersion. The dispersion is slowly sprayed into a blend of the lactose and microcrystalline cellulose. The resulting composition is then dried and milled to form a granulation, which is then combined with the croscarmellose sodium and magnesium stearate. This blend is then used to fill capsules using appropriate equipment.

EXAMPLE 3

Enhanced Bioavailability of Oral 17β-estradiol When Administered as its 3-Acetate Ester According to the Invention A study was performed to compare the bioavailability of 17β-estradiol and 17β-estradiol-3-acetate tablets following oral administration to postmenopausal female volunteers. The study was an open-label, single-dose, randomized, crossover, bioavailability study in nine healthy postmenopausal women volunteers. Each volunteer received: A) one tablet of 1.152-mg 17β-estradiol-3-acetate tablet (equivalent to 1.0 mg of 17β-estradiol), prepared in a manner substantially similar to Example 1; and B) one tablet of 1-mg micronized 17β-estradiol (Estrace® Tablets); each treatment was separated by a one-week washout period. Data from eight subjects were evaluable.

Mean serum estradiol concentrations following administration of one 17β-estradiol-3-acetate tablet were higher than those following administration of one micronized 17β-estradiol tablet. Mean estradiol and estrone pharmacokinetic parameters following administration of one 17β-estradiol-3-acetate tablet and one estradiol tablet are summarized in Table 1. Comparison of treatments was based on ratio of least square means from analysis of variance and ratio of individual subject parameter values, e.g. ratio=(AUCtreatment A)/(AUCtreatment B). A summary of mean ratios is given in Table 2.

Following administration of treatment A, serum 17β-estradiol concentrations increased rapidly (Tmax=2-3 hours), then decreased rapidly to relatively constant 17β-estradiol concentrations over 3 to 24 hours postdose. Following administration of micronized 17β-estradiol, serum 17β-estradiol increased slowly over the first six hours to relatively constant concentrations over 6 to 24 hours postdose.

Cmax values following administration of one 17β-estradiol-3-acetate tablet were two times higher than those following administration of one micronized 17β-estradiol tablet. Relative bioavailability as indicated by ratio of AUC values was 15% higher for 17β-estradiol-3-acetate as compared to micronized 17β-estradiol.

Serum estradiol concentration-time profiles following administration of 17β-estradiol-3-acetate and micronized 17β-estradiol suggest differences in absorption. The shape of the profiles following 17β-estradiol-3-acetate administration indicate that it is rapidly absorbed and hydrolyzed to 17β-estradiol in vivo while the profile for estradiol administration indicates that 17β-estradiol itself is more slowly absorbed from micronized estradiol. Similarity of profiles at later times (>6 hours) following 17β-estradiol-3-acetate administration and micronized 17β-estradiol administration suggests that disposition and elimination are not affected by administration of the 3-acetate ester of the naturally occurring hormone The reasons for the surprising improved bioavailability (higher Cmax and AUC values) seen with this example formulation of the invention are not clear but, without being bound by theory, may be related to the higher aqueous solubility characteristics of 17β-estradiol-3-acetate and a consequential effect on membrane permeability. Without being bound by theory it could also be due to an unexpected reduction in hepatic first pass metabolism when 17β-estradiol is administered orally as its 3-acetate ester.

TABLE 1

Summary of 17β-Estradiol Pharmacokinetic Parameters Following Oral Administration of One 17β-estradiol-3-acetate and One 17β-estradiol Tablets (n = 8);

| Parameter | One 17β-Estradiol-3-acetate Tablet Mean (% RSD) | One 17β-Estradiol Tablet Mean % RSD |
| --- | --- | --- |
| Cmax | 54.6 (48) | 25.9 (24) |
| tmax | 1.9 (141) | 10.1 (54) |
| AUC (0-tldc) | 913.8 (25) | 793.6 (20) |

Cmax = Maximum serum concentration (pg/mL)
tmax = Time of Cmax (hr)
AUC(0-tldc) = Area under concentration-time profile (pg hr/mL) from time zero to time tldc, time of last determinable concentration

What is claimed is:

1. A method of treating a human female having a deficiency of 17β-estradiol comprising the step of orally administering to said human female a solid dosage unit comprising a therapeutically effective amount of 17β-estradiol-3-acetate and a pharmaceutically acceptable carrier, wherein the percent moisture of said dosage unit is less than or equal to 5%, and the amount of 17β-estradiol-3-acetate is from about 0.1 to about 10 mg as estradiol equivalent, wherein the oral solid dosage unit further comprises a pharmaceutically acceptable inhibitor of ester hydrolysis that is acetic acid.

2. The method according to claim 1, wherein said dosage unit further comprises one or more additional medicaments.

3. The method according to claim 2, wherein at least one additional medicament has progestational activity.

4. The method according to claim 1, wherein the dosage unit is a tablet, capsule, powder, lozenge, troche or suspension.

5. The method according to claim 4, wherein the dosage unit is a tablet or capsule.

* * * * *

UNITED STATES PATENT AND TRADEMARK OFFICE
CERTIFICATE OF CORRECTION

PATENT NO. : 7,572,779 B2 Page 1 of 1
APPLICATION NO. : 10/833997
DATED : August 11, 2009
INVENTOR(S) : Aloba et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1381 days.

Signed and Sealed this

Fourth Day of January, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,572,779 B2 | Page 1 of 1 |
| APPLICATION NO. | : 10/833997 | |
| DATED | : August 11, 2009 | |
| INVENTOR(S) | : Oluwole T. Aloba et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1381 days.

Signed and Sealed this

Fifteenth Day of February, 2011

David J. Kappos
*Director of the United States Patent and Trademark Office*